(12) United States Patent
Zhang

(10) Patent No.: US 9,113,803 B2
(45) Date of Patent: Aug. 25, 2015

(54) MAGNETOENCEPHALOGRAPHY METER FOR MEASURING NEUROMAGNETISM

(71) Applicant: Sumitomo Heavy Industries, Ltd., Tokyo (JP)

(72) Inventor: Yanping Zhang, Tokyo (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 14/085,371

(22) Filed: Nov. 20, 2013

(65) Prior Publication Data

US 2014/0121491 A1    May 1, 2014

Related U.S. Application Data

(63) Continuation of application No. PCT/JP2012/060159, filed on Apr. 13, 2012.

(30) Foreign Application Priority Data

Jul. 13, 2011  (JP) .................................. 2011-154881

(51) Int. Cl.
 *A61B 5/04* (2006.01)
 *A61B 5/00* (2006.01)
 *G01R 33/26* (2006.01)

(52) U.S. Cl.
 CPC ........... *A61B 5/04008* (2013.01); *A61B 5/6803* (2013.01); *G01R 33/26* (2013.01)

(58) Field of Classification Search
 CPC . A61B 5/04008; A61B 5/6803; A61B 5/0408
 See application file for complete search history.

(56) References Cited

U.S. PATENT DOCUMENTS

| 2005/0206377 A1 | 9/2005 | Romalis et al. |
| 2007/0167723 A1* | 7/2007 | Park et al. ..................... 600/409 |
| 2011/0031969 A1* | 2/2011 | Kitching et al. .............. 324/304 |

FOREIGN PATENT DOCUMENTS

| JP | 2010-088592 A | 4/2010 |
| JP | 2011-007660 A | 1/2011 |
| JP | 2011-106950 A | 6/2011 |
| WO | WO-2007/078889 A2 | 7/2007 |
| WO | WO-2008/127720 A2 | 10/2008 |

OTHER PUBLICATIONS

International Search Report issued in Application No. PCT/JP2012/060159, dated Jun. 12, 2012.

(Continued)

*Primary Examiner* — Amanda Lauritzen Moher
(74) *Attorney, Agent, or Firm* — Fishman Stewart Yamaguchi PLLC

(57) ABSTRACT

Disclosed is a magnetoencephalography meter which includes a plurality of optical pumping magnetometers which are arranged in a helmet shape to cover the head of the subject. Each optical pumping magnetometer has a vapor cell which is filled with alkali metal atoms and is arranged substantially in parallel to the surface of the head of the subject, a laser light emission unit that emits laser light in a direction toward the head of the subject and causes laser light to enter the vapor cell, a reflection unit that reflects laser light passed through the vapor cell in a direction away from the head of the subject which is a direction substantially perpendicular to the surface of the head of the subject, and a polarization change detection unit that receives laser light reflected by the reflection unit and detects change in polarization of laser light.

5 Claims, 5 Drawing Sheets

(56) References Cited

OTHER PUBLICATIONS

International Preliminary Report on Patentability issued in Application No. PCT/JP2012/060159, dated Jan. 14, 2014.

Peter D. D. Schwindt et al., "Chip-scale atomic magnetometer," Applied Physics Letters, Dec. 27, 2004, vol. 85, No. 26, pp. 6409-6411 (3 sheets).

* cited by examiner

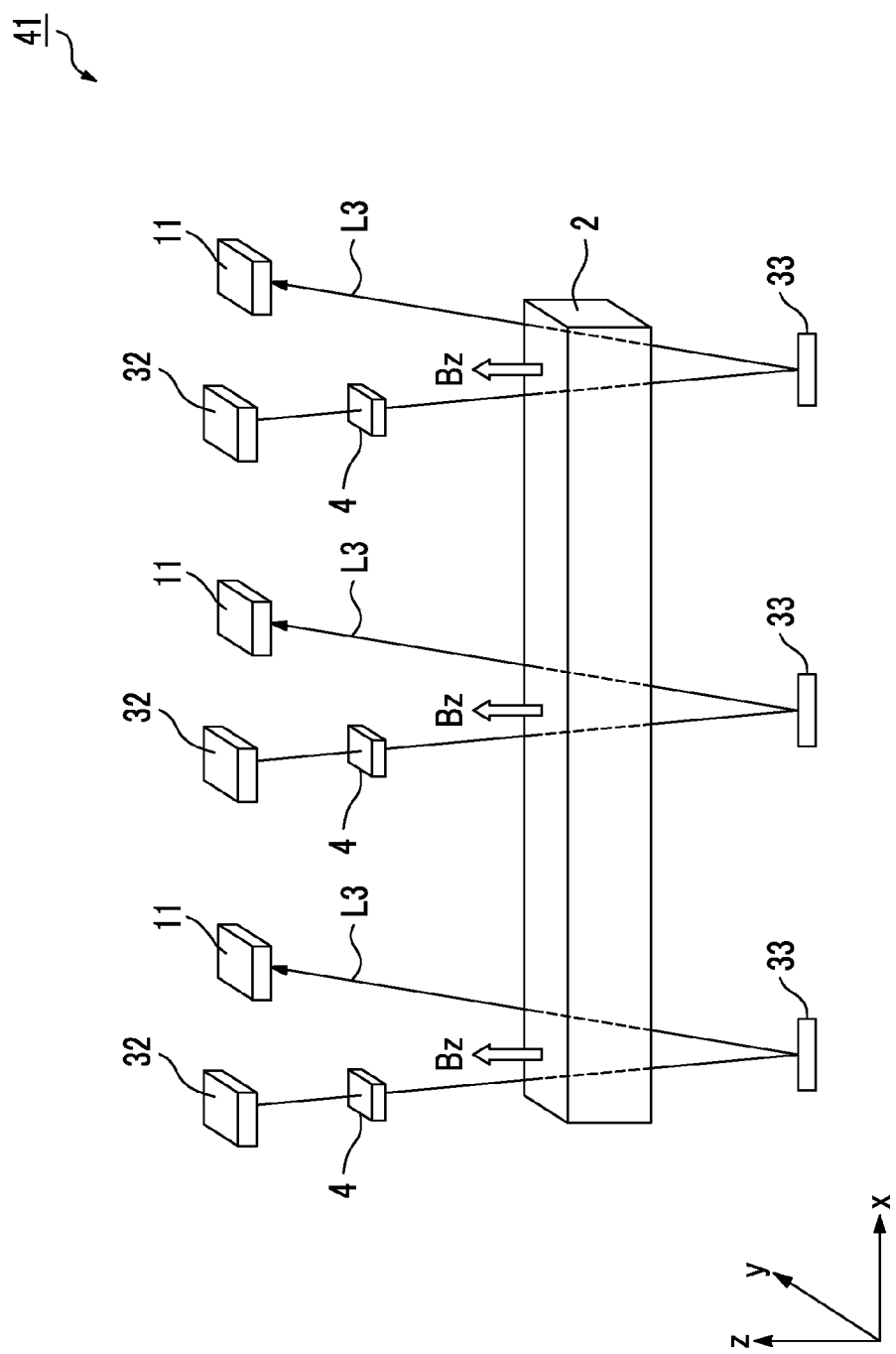

MAGNETOENCEPHALOGRAPHY METER FOR MEASURING NEUROMAGNETISM

INCORPORATION BY REFERENCE

Priority is claimed to Japanese Patent Application No. 2011-154881, filed Jul. 13, 2011, and International Patent Application No. PCT/JP2012/060159, the entire content of each of which is incorporated herein by reference.

BACKGROUND

1. Technical Field

The present invention relates to a magnetoencephalography meter and a neuromagnetism measuring method.

2. Description of the Related Art

In recent years, as a SQUID sensor-alternative high-sensitivity magnetometer, an optical pumping magnetometer using an alkali metal has been developed. Since the optical pumping magnetometer does not require a cooling function, and allows significant reduction in running cost against the SQUID sensor, the application to a magnetoencephalography meter or the like is expected.

In order to precisely measure a neuromagnetic field using the optical pumping magnetometer and to improve measurement sensitivity, multiple small optical pumping magnetometers should be used. Accordingly, for example, as described in P. D. D. Schwindt et al., "Chip-scale atomic magnetometer", App. Phys. Lett. Vol. 85, No. 26, pp. 6409-6411 (2004), an optical pumping magnetometer having volume of 12 mm$^3$ is produced by way of trial. The optical pumping magnetometer described in P. D. D. Schwindt et al., "Chip-scale atomic magnetometer", App. Phys. Lett. Vol. 85, No. 26, pp. 6409-6411 (2004) has the following configuration. A vertical resonator surface light-emitting laser is provided at a position separated upward from a substrate, a vapor cell filled with rubidium vapor is provided below the vertical resonator surface light-emitting laser, and a photodiode is provided below the vapor cell. The photodiode is provided on the top surface of the substrate, and is configured to have a light receiving unit at a position where light emitted from the vertical resonator surface light-emitting laser and passed through the vapor cell is received.

SUMMARY

According to an embodiment of the invention, there is provided a magnetoencephalography meter which measures neuromagnetism of the head of a subject. The magnetoencephalography meter includes a plurality of optical pumping magnetometers which are arranged in a helmet shape to cover the head of the subject. Each optical pumping magnetometer has a vapor cell that is filled with alkali metal atoms and is arranged substantially in parallel to the surface of the head of the subject, a laser light emission unit that emits laser light in a direction toward the head of the subject which is a direction substantially perpendicular to the surface of the head of the subject and causes laser light to enter the vapor cell, a reflection unit which reflects laser light passed through the vapor cell in a direction away from the head of the subject which is a direction substantially perpendicular to the surface of the head of the subject, and a polarization change detection unit that receives laser light reflected by the reflection unit and detects change in polarization of laser light.

According to another embodiment of the invention, there is provided a neuromagnetism measuring method which measures neuromagnetism of the head of a subject. A plurality of optical pumping magnetometers which are arranged in a helmet shape to cover the head of the subject are used, and in each optical pumping magnetometer, a vapor cell arranged substantially in parallel to the surface of the head of the subject is filled with alkali metal atoms, laser light is emitted in a direction toward the head of the subject which is a direction substantially perpendicular to the surface of the head of the subject and enters the vapor cell, laser light passed through the vapor cell is reflected in a direction away from the head of the subject which is a direction substantially perpendicular to the surface of the head of the subject, and reflected laser light is received and change in polarization of laser light is detected to measure neuromagnetism of the subject.

BRIEF DESCRIPTION OF THE DRAWINGS

FIG. 5 is a perspective view showing another optical pumping magnetometer which constitutes the magnetoencephalography meter according to another embodiment of the invention.

DETAILED DESCRIPTION

Figure 1:
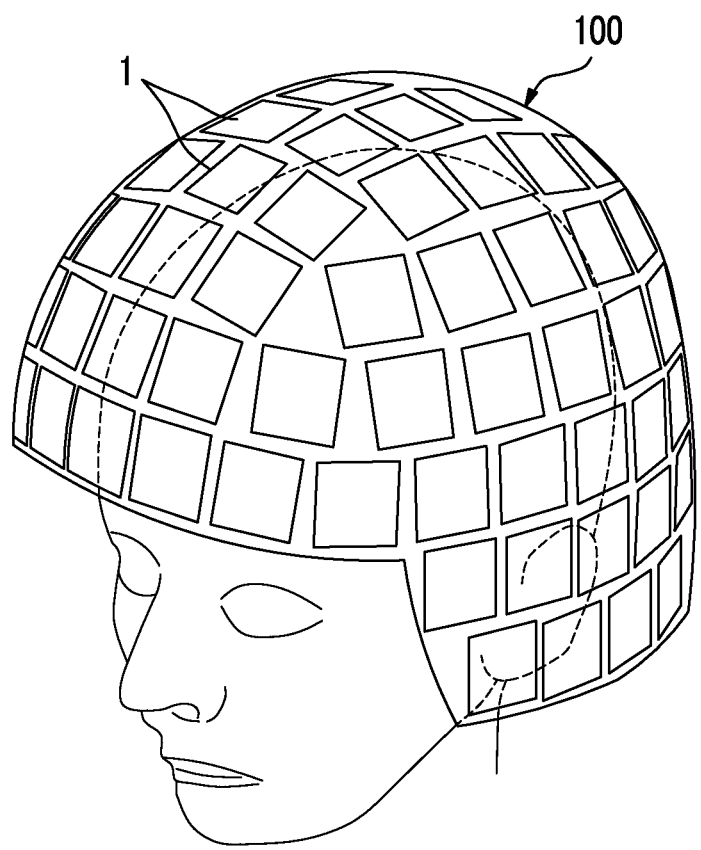
FIG. 1 is a schematic perspective view showing a magnetoencephalography meter according to one embodiment of the invention.

When the optical pumping magnetometer is arranged in a flat manner on the head of a subject, since the direction of a magnetic field to be detected by the optical pumping magnetometer does not match the direction of neuromagnetism from the subject at a certain location, it is not possible to measure neuromagnetism with high precision.

As described above, if a light receiving element, such as a photodiode, is provided on the substrate, an electrical wire should be drawn from the outside to the light receiving element on the substrate. Accordingly, when multiple optical pumping magnetometers are arranged in parallel to produce a magnetoencephalography meter, it is not possible to produce a magnetoencephalography meter with simple configuration.

There is a need for a low-cost and high-precision magnetoencephalography meter with simple configuration and a neuromagnetism measuring method.

With these, a plurality of optical pumping magnetometers are arranged in a helmet shape to cover the head of the subject, and the vapor cell which constitutes each optical pumping magnetometer is arranged substantially in parallel to the surface of the head of the subject. Accordingly, it becomes possible to allow the direction of a magnetic field to be detected by the optical pumping magnetometer to match the direction of neuromagnetism from the subject, and neuromagnetism can be measured with high precision. Laser light is emitted in the direction toward the head of the subject which is the direction substantially perpendicular to the surface of the head of the subject and enters the vapor cell, and laser light whose optical path is changed in a direction away from the head of the subject which is the direction substantially perpendicular to the surface of the head of the subject is received.

For this reason, it is not necessary to draw an electrical wire to a light receiving element receiving laser light from the outside to a position near the head of the subject. Therefore, when arranging multiple optical pumping magnetometers in parallel to produce a magnetoencephalography meter, it is possible to produce a magnetoencephalography meter with simple configuration.

In the magnetoencephalography meter, the vapor cell may pass through a plurality of components of laser light. With this, since the vapor cell is expanded, such that the single vapor cell can be used commonly to a plurality of components of laser light, it is possible to reduce variation in vapor density in a region through which each component of laser light passes and to increase measurement precision.

The vapor cell may be expanded insofar as a given degree of flatness is maintained. With this, since the number of cells can be decreased, it is possible to reduce variation in vapor density and to increase measurement precision.

Both the laser light emission unit and the polarization change detection unit may be provided on the vapor cell. With this, the laser light emission unit, the polarization change detection unit, and the vapor cell can be handled as an integrated unit, handling is facilitated, and the magnetoencephalography meter is reduced in size.

In each optical pumping magnetometer, the laser light emission unit may separately have a pump light emission unit that emits pump light and a probe light emission unit that emits probe light, the pump light emission unit may cause pump light to enter the vapor cell in a first direction parallel to the surface of the head of the subject, the probe light emission unit may cause probe light to enter the vapor cell in a second direction perpendicular to the first direction which is a direction parallel to the surface of the head of the subject, the reflection unit may reflect probe light passed through the vapor cell, and the polarization change detection unit may detect change in polarization of probe light reflected by the reflection unit.

With this, pump light enters the vapor cell in the first direction parallel to the surface of the head of the subject, and laser light enters the vapor cell as probe light in the second direction perpendicular to the first direction which is the direction parallel to the surface of the head of the subject. Therefore, it is possible to measure neuromagnetism in a direction perpendicular to both the first direction and the second direction, that is, a direction perpendicular to the surface of the head of the subject.

The laser light emission unit may cause laser light to enter the vapor cell in a direction toward the head of the subject which is a direction substantially perpendicular to the surface of the head of the subject.

With this, laser light enters in the direction toward the head of the subject which is the direction substantially perpendicular to the surface of the head of the subject, then, laser light is reflected in the direction substantially perpendicular to the surface of the head of the subject and away from the head of the subject, laser light is received, and change in polarization of laser light is detected. For this reason, it is not necessary to prepare two light sources of pump light and probe light, thereby producing a low-cost and space-saving magnetoencephalography meter.

According to the embodiments of the invention, a low-cost and high-precision magnetoencephalography meter with simple configuration and a neuromagnetism measuring method are obtained.

Hereinafter, a preferred embodiment of a magnetoencephalography meter according to the invention will be described referring to the drawings. In the drawings, the same parts are represented by the same reference numerals, and overlapping description will be omitted.

(Embodiment)

FIG. 1 is a schematic perspective view showing a magnetoencephalography meter according to one embodiment of the invention. The magnetoencephalography meter measures neuromagnetism of the head of a human.

As shown in FIG. 1, a magnetoencephalography meter 100 includes a plurality of optical pumping magnetometers 1. Each optical pumping magnetometer 1 has a vapor cell 2 (see FIG. 2). Multiple vapor cells 2 are arranged in a helmet shape to cover the head of the subject (to follow the surface shape of the head).

Figure 2:
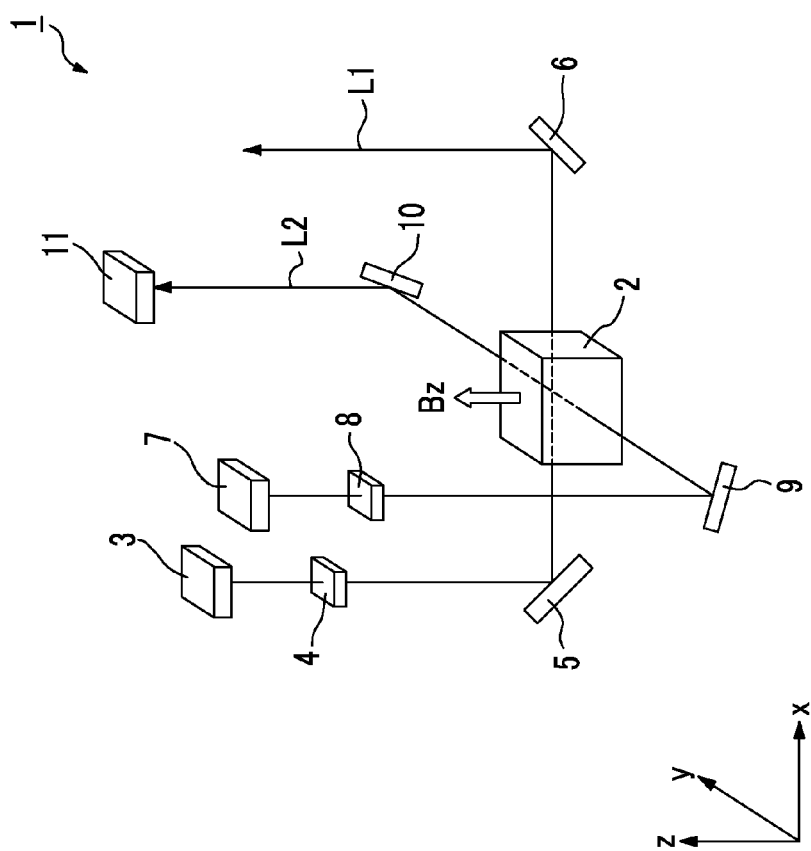
FIG. 2 is a perspective view showing an optical pumping magnetometer which constitutes the magnetoencephalography meter according to one embodiment of the invention.

FIG. 2 is a perspective view showing the optical pumping magnetometer 1 according to one embodiment of the invention.

The optical pumping magnetometer 1 has a vapor cell 2, a pump light laser (pump light emission unit) 3, a polarizer 4, a mirror 5, a mirror 6, a probe light laser (probe light emission unit) 7, a polarizer 8, a mirror 9, a mirror (reflection unit) 10, and a photodiode (polarization change detection unit) 11. The head of the subject is on the negative side of a z-axis direction when viewed from the optical pumping magnetometer 1. The surface of the head of the subject is parallel to an xy plane and perpendicular to the z-axis direction. Since neuromagnetism of the human primarily has a component in a direction perpendicular to the surface of the head, neuromagnetism of the subject primarily has a component in the z-axis direction.

The vapor cell 2 is a hollow body which is formed of a transparent material, such as glass or quartz. Inside the vapor cell 2, an alkali metal, for example, an alkali metal, such as potassium, rubidium, or cesium, is filled. As buffer gas for preventing alkali metal atoms from colliding against the wall of the vapor cell 2, rare gas, for example, helium or the like is also filled inside the vapor cell 2. As quenching gas for prevention of fluorescence, for example, gas, such as nitrogen, is also filled inside the vapor cell 2. The vapor cell 2 is heated by a heater which is provided in contact with the wall of the vapor cell 2 or by causing hot air generated at a location separated from the vapor cell 2 to flow around the vapor cell 2. The higher the density of vapor of the vapor cell 2, the more sensitivity of neuromagnetism measurement is improved. However, when taking practicality into consideration, the temperature of the cell can be 100 degrees C. to about 200 degrees C. In order to maintain the temperature of the vapor cell 2 and to protect the head of the subject, the entire vapor cell 2 is covered with a thermal insulator. The vapor cell 2 can be expanded insofar as a given degree of flatness is maintained. That is, the vapor cell 2 can be expanded within a range in which the flat surface of the vapor cell 2 and the surface of the head of the subject can be parallel to each other.

The pump light laser 3 irradiates pump light L1 onto the vapor cell 2. Pump light L1 optically pumps the alkali metal inside the vapor cell 2. The pump light laser 3 emits light having a wavelength to optically pump the alkali metal inside the vapor cell 2. The pump light laser 3 emits pump light L1 in a negative direction of the z-axis direction. The negative direction of the z-axis direction is a direction toward the head of the subject which is a direction perpendicular to the surface of the head of the subject.

The polarizer 4 circularly polarizes the polarization state of pump light L1 emitted from the pump light laser 3. Specifically, a $\lambda/4$ plate which circularly polarizes linearly polarized light, or the like is used.

The mirror 5 changes the optical path of pump light L1 passed through the polarizer 4, and causes pump light L1 to enter the vapor cell 2.

The mirror 6 changes the optical path of pump light L1 passed through the vapor cell 2 in a direction away from the head of the subject.

The probe light laser 7 irradiates probe light L2 onto the vapor cell 2. The probe light laser 7 emits probe light L2 in the negative direction of the z-axis direction. The negative direction of the z-axis direction is a direction toward the head of the subject which is a direction perpendicular to the surface of the head of the subject.

The polarizer 8 linearly polarizes the polarization state of probe light L2 emitted from the probe light laser 7.

The mirror 9 changes the optical path of probe light L2 passed through the polarizer 8 and causes probe light L2 to enter the vapor cell 2.

The mirror 10 changes the optical path of probe light L2 passed through the vapor cell 2 and causes probe light L2 to enter the photodiode 11. The mirror 10 reflects probe light L2 in a positive direction of the z-axis direction. The positive direction of the z-axis direction is a direction away from the head of the subject which is a direction perpendicular to the surface of the head of the subject.

The photodiode 11 is a light receiving element which receives probe light L2 reflected by the mirror 10. The photodiode 11 can detect the rotation angle of the plane of polarization of probe light L2.

All the pump light laser 3, the probe light laser 7, and the photodiode 11 are provided on the vapor cell 2.

As described below, the optical pumping magnetometer 1 configured as above measures a magnetic filed by a spin exchange relaxation-free (SERF) method.

When measuring neuromagnetism of the subject, the vapor cell 2 is heated in advance by a heater which is provided in contact with the wall of the vapor cell 2 or by causing hot air generated at a location separated from the vapor cell 2 to flow around the vapor cell 2. Accordingly, the alkali metal atoms inside the vapor cell 2 reach predetermined density.

Next, pump light L1 is emitted from the pump light laser 3 in the negative direction of the z-axis direction, the polarization state of emitted pump light L1 is circularly polarized by the polarizer 4, and circularly polarized pump light L1 is reflected in a positive direction (first direction) of an x-axis direction by the mirror 5 and enters the vapor cell 2. The x-axis direction is a direction parallel to the surface of the head of the subject. In general, the mirror 5 differs between reflectance against s-wave (light whose electric field component is perpendicular to the plane of entrance) and reflectance against p-wave (light whose electric field component is parallel to the plane of entrance). Accordingly, after pump light L1 is reflected, the polarization state of pump light L1 should be circularly polarized when entering the vapor cell 2, and the s-wave component and the p-wave component of pump light L1 entering the mirror 5 are appropriately adjusted. The same applies to the mirror 9 described below.

If pump light L1 which is circularly polarized light enters the vapor cell 2, the alkali metal atoms inside the vapor cell 2 are optically pumped, and the atomic spins are arranged in the same direction.

Pump light L1 passes through the vapor cell 2 and is reflected in the positive direction of the z-axis direction by the mirror 6.

In a state where the alkali metal inside the vapor cell 2 is optically pumped in the above-described manner, probe light L2 is emitted from the probe light laser 7 in the negative direction of the z-axis direction, the polarization state of emitted probe light L2 is linearly polarized by the polarizer 8, and linearly polarized probe light L2 is reflected in a positive direction (second direction) of a y-axis direction by mirror 9 and enters the vapor cell 2. The y-axis direction is a direction perpendicular to the x-axis direction which is a direction parallel to the surface of the head of the subject.

In the vapor cell 2, circularly polarized pump light L1 enters in the x-axis direction, and linearly polarized probe light L2 enters in the y-axis direction. In this case, the plane of polarization of probe light L2 rotates by an angle according to a magnetic field Bz in a direction perpendicular to both pump light L1 and probe light L2, that is, in the z-axis direction.

Probe light L2 passes through the vapor cell 2, is reflected in the positive direction of the z-axis direction by the mirror 10, and is then received by the photodiode 11. A current which flows when the photodiode 11 receives light changes according to the rotation angle of the plane of polarization of probe light L2. Accordingly, the rotation angle of the plane of polarization of probe light L2, that is, change in polarization can be detected by the photodiode 11, and the magnetic field Bz in the z-axis direction in the vapor cell 2, that is, neuromagnetism of the subject can be measured from the rotation angle of the plane of polarization of probe light L2.

As described above, in the magnetoencephalography meter 100 of this embodiment, since a plurality of optical pumping magnetometers 1 are arranged in a helmet shape to cover the head of the subject, and the vapor cell 2 which constitutes each optical pumping magnetometer 1 is arranged substantially in parallel to the surface of the head of the subject, the direction of the magnetic field to be detected by the optical pumping magnetometer 1 matches the direction of neuromagnetism from the subject, thereby measuring neuromagnetism with high precision. In the optical pumping magnetometer 1, pump light L1 which is circularly polarized light enters the vapor cell 2 in the x-axis direction parallel to the surface of the head of the subject, and probe light L2 which is linearly polarized light enters the vapor cell 2 in the y-axis direction parallel to the surface of the head of the subject and perpendicular to the x-axis direction. Accordingly, neuromagnetism in a direction perpendicular to both the x-axis direction and the y-axis direction, that is, in a direction perpendicular to the surface of the head of the subject can be measured with high precision.

Probe light L2 is emitted in the negative direction of the z-axis direction which is a direction perpendicular to the surface of the head of the subject and a direction toward the head of the subject, the polarization state is linearly polarized, linearly polarized probe light L2 enters the vapor cell 2, the optical path of probe light L2 is changed in the positive direction of the z-axis direction which is a direction perpendicular to the surface of the head of the subject and a direction away from the head of the subject, and probe light L2 is received by the photodiode 11. For this reason, it is not necessary to draw an electrical wire to the photodiode 11 from the outside to a position near the head of the subject, and when arranging multiple optical pumping magnetometers 1 to produce the magnetoencephalography meter 100, it is possible to produce the magnetoencephalography meter 100 with simple configuration.

Since the vapor cell 2 is expanded insofar as a given degree of flatness is maintained, the number of vapor cells 2 can be decreased, thereby reducing variation in vapor density and increasing measurement precision.

Since all the pump light laser 3, the probe light laser 7, and the photodiode 11 are provided on the vapor cell 2, the pump light laser 3, the probe light laser 7, the photodiode 11, and the vapor cell 2 can be handled as an integrated unit, handling is facilitated, and the magnetoencephalography meter 100 can be reduced in size.

Figure 3:
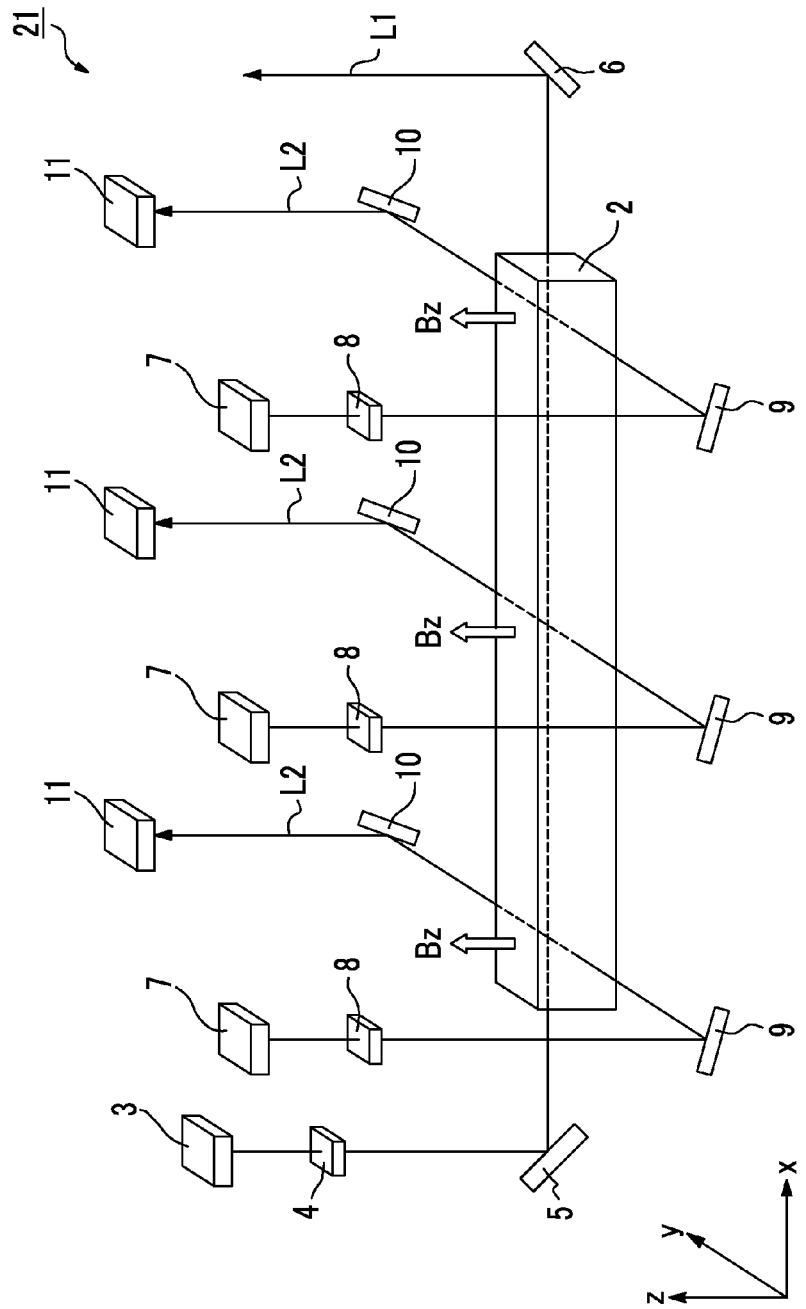
FIG. 3 is a perspective view showing another optical pumping magnetometer which constitutes the magnetoencephalography meter according to one embodiment of the invention.

FIG. 3 is a perspective view showing another optical pumping magnetometer 21 according to one embodiment of the invention.

The optical pumping magnetometer 21 has the following difference from the optical pumping magnetometer 1. That is, although only one component of probe light L2 passes through the vapor cell 2 in the optical pumping magnetometer 1, in the optical pumping magnetometer 21, the vapor cell 2 is expanded insofar as a given degree of flatness is maintained such that a plurality of components of probe light L2 can pass therethrough. In this way, how much the vapor cell 2 is expanded is limited by the degree of flatness of a region to be measured. That is, if the vapor cell 2 is excessively expanded, since a region to be measured is curved, the bottom surface of the vapor cell 2 and the region to be measured are not in parallel to each other, and neuromagnetism measurement cannot be performed. The size of the vapor cell 2 is limited by attenuation of intensity of pump light L1 emitted from the pump light laser 3, uniformity of the density of alkali metal vapor inside the vapor cell 2, and the like. From other points, the configuration and function of the optical pumping magnetometer 21 are the same as the optical pumping magnetometer 1.

In the optical pumping magnetometer 21 configured as above, the same effects as the optical pumping magnetometer 1 can be obtained, and in addition, the number of pump light lasers 3 can be reduced and lower cost can be achieved.

In the optical pumping magnetometer 21, unlike the optical pumping magnetometer 1 in which a plurality of vapor cells 2 are provided for a plurality of components of probe light L2, a single large vapor cell 2 is provided. For this reason, since the single vapor cell 2 can be used commonly to a plurality of components of probe light, it is possible to reduce variation in vapor density in a region through which each component of probe light passes and to increase measurement precision.

Since the vapor cell 2 is expanded insofar as a given degree of flatness is maintained, the number of cells can be decreased, thereby reducing variation in vapor density and increasing measurement precision.

(Another Embodiment)

Figure 4:
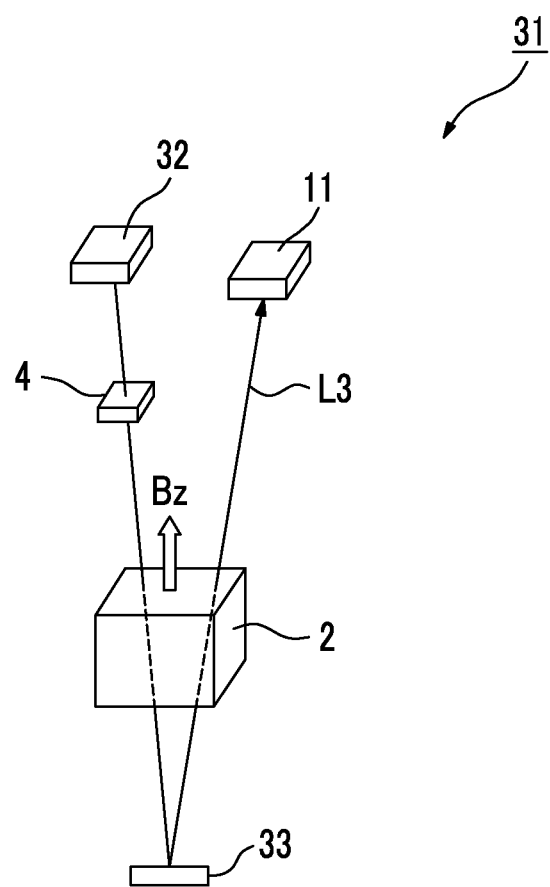
FIG. 4 is a perspective view showing an optical pumping magnetometer which constitutes a magnetoencephalography meter according to another embodiment of the invention.

FIG. 4 is a perspective view showing an optical pumping magnetometer 31 according to another embodiment of the invention.

The optical pumping magnetometer 31 of this embodiment has the following difference from the optical pumping magnetometer 1 of the foregoing embodiment. That is, although the optical pumping magnetometer 1 of the foregoing embodiment measures neuromagnetism by the SERF method, in the optical pumping magnetometer 31, neuromagnetism is measured using a so-called nonlinear Faraday rotation phenomenon. For this reason, the optical pumping magnetometer 31 of this embodiment has the following configuration different from the optical pumping magnetometer 1 of the foregoing embodiment.

The optical pumping magnetometer 31 of this embodiment has a laser (laser light emission unit) 32, a polarizer 8, a vapor cell 2, a mirror (reflection unit) 33, and a photodiode (polarization change detection unit) 11. The head of the subject is on the negative side of the z-axis direction when viewed from the optical pumping magnetometer 31. The surface of the head of the subject is parallel to the xy plane and perpendicular to the z-axis direction.

The laser 32 emits laser light L3 in a direction toward the head of the subject, which is a direction substantially perpendicular to the surface of the head of the subject, and a direction substantially close to the negative direction of the z axis. The direction substantially close to the negative direction of the z axis is a direction in which laser light L3 generates a nonlinear Faraday rotation phenomenon by a magnetic field in the z-axis direction, and a direction in which, when the optical pumping magnetometers 31 are arranged in parallel along the surface of the head of the subject, there is no interference with the position of the laser 32 or the photodiode 11. The laser 32 causes laser light L3 to enter the vapor cell 2 through the polarizer 8 in the direction substantially close to the negative direction of the z-axis direction.

The polarizer 8 causes laser light L3 to enter the vapor cell 2 in a direction substantially perpendicular to the surface of the head of the subject and toward the head of the subject, specifically, in a direction substantially close to the negative direction of the z axis.

The mirror 33 reflects laser light L3 passed through the vapor cell 2 in a direction away from the head of the subject which is a direction perpendicular to the surface of the head of the subject, specifically, in a direction substantially close to the positive direction of the z-axis direction.

Both the laser 32 and the photodiode 11 are provided on the vapor cell 2.

As described below, the optical pumping magnetometer 31 configured as above measures a magnetic field using a nonlinear Faraday rotation phenomenon.

Similarly to the optical pumping magnetometer 1, when measuring neuromagnetism of the subject, the vapor cell 2 is heated in advance by a heater which is provided in contact with the wall of the vapor cell 2 or by causing hot air generated at a location separated from the vapor cell 2 to flow around the vapor cell 2.

Next, laser light L3 is emitted from the laser 32 in the direction substantially close to the negative direction of the z axis, the polarization state of laser light L3 is linearly polarized by the polarizer 8, and linearly polarized laser light L3 enters the vapor cell 2 in the direction substantially close to the negative direction of the z axis.

Laser light L3 travels inside the vapor cell 2 in the direction substantially close to the negative direction of the z axis. At this time, the plane of polarization of laser light L3 rotates by an angle according to the magnetic field Bz in the z-axis direction by the non-linear Faraday rotation phenomenon.

Laser light L3 passes through the vapor cell 2, is reflected in the positive direction of the z-axis direction by the mirror 33, and is then received by the photodiode 11. Similarly to the optical pumping magnetometer 1 of the foregoing embodiment, the rotation angle of the plane of polarization of laser light L3, that is, change in polarization is detected by the photodiode 11, and the magnetic field in the z-axis direction in the vapor cell 2, that is, neuromagnetism of the subject is measured by the rotation angle.

With the magnetoencephalography meter 100 using the optical pumping magnetometer 31 described above, the direction of the magnetic field to be detected by the optical pumping magnetometer 31 matches the direction of neuromagnetism from the subject, and neuromagnetism can be measured with high precision.

The action of the optical pumping magnetometer 31 having a plurality of vapor cells 2 is the same as the optical pumping magnetometer 1. Therefore, it is not necessary to draw an electric wire to the photodiode 11 from the outside to a position near the head of the subject, thereby producing the magnetoencephalography meter 100 with simple configuration.

Since the vapor cell 2 is expanded insofar as a given degree of flatness is maintained, the number of cells can be decreased, thereby reducing variation in vapor density and increasing measurement precision.

Since both the laser 32 and the photodiode 11 are provided on the vapor cell 2, the laser 32, the photodiode 11, and the vapor cell 2 can be handled as an integrated unit, handling is facilitated, and the magnetoencephalography meter 100 can be reduced in size.

In the optical pumping magnetometer 31, laser light L3 enters in the direction toward the head of the subject which is the direction substantially perpendicular to the surface of the head of the subject, laser light L3 is reflected in the direction substantially perpendicular to the surface of the head of the subject and away from the head of the subject, laser light L3 is received, and change in polarization of laser light L3 is detected. For this reason, it is not necessary to prepare two light sources of pump light and probe light, thereby producing a low-cost and space-saving magnetoencephalography meter.

FIG. 5 is a perspective view showing another optical pumping magnetometer 41 according to another embodiment of the invention.

The optical pumping magnetometer 41 has the following difference from the optical pumping magnetometer 31. That is, although only one component of laser light L3 passes through the vapor cell 2 in the optical pumping magnetometer 31, in the optical pumping magnetometer 41, the vapor cell 2 is expanded insofar as a given degree of flatness is maintained such that a plurality of components of laser light L3 can pass therethrough. From other points, the configuration and function of the optical pumping magnetometer 41 are the same as the optical pumping magnetometer 31.

Accordingly, the optical pumping magnetometer 41 has the same functional effects as the optical pumping magnetometer 31. The vapor cell 2 is expanded such that a plurality of components of laser light L3 pass through the vapor cell 2, and the single vapor cell 2 can be used commonly to a plurality of components of laser light L3. For this reason, it is possible to reduce variation in vapor density in a region through which each component of laser light passes and to increase measurement precision.

Although the invention has been specifically described on the basis of the embodiments, the invention is not limited to the foregoing embodiments. For example, in the foregoing embodiments, although the photodiode 11 is used as polarization change detection unit, the rotation angle of the plane of polarization of probe light L2 or laser light L3 may be detected by various known methods.

It should be understood that the invention is not limited to the above-described embodiment, but may be modified into various forms on the basis of the spirit of the invention. Additionally, the modifications are included in the scope of the invention.

What is claimed is:

1. A magnetoencephalography meter which measures neuromagnetism of a head of a subject, the magnetoencephalography meter comprising:
a plurality of optical pumping magnetometers which are arranged in a helmet shape configured to cover the head of the subject,
wherein each optical pumping magnetometer comprises:
a vapor cell that is filled with alkali metal atoms and is arranged in parallel to the surface of the head of the subject such that a local z-axis of each optical pumping magnetometer is perpendicular to a surface of the head of the subject,
a laser light emission unit that is configured to emit a laser light in a −z direction parallel to the local z-axis toward the head of the subject and to cause the laser light to enter the vapor cell,
a reflection unit that is configured to reflect the laser light passed through the vapor cell in a +z direction parallel to the local z-axis away from the head of the subject, and
a polarization change detection unit that is configured to receive the laser light reflected by the reflection unit and to detect a change in polarization of the laser light.

2. The magnetoencephalography meter according to claim 1,
wherein, for each of the optical pumping magnetometers, the laser light emission unit, the reflection unit and the polarization change detection unit are respectively provided in plural numbers.

3. The magnetoencephalography meter according to claim 1,
wherein both the laser light emission unit and the polarization change detection unit are provided on the vapor cell.

4. The magnetoencephalography meter according to claim 1,
wherein, in the optical pumping magnetometer,
the laser light emission unit comprises a pump light emission unit that is configured to emit a pump light and a probe light emission unit that is configured to emit a probe light,
the pump light emission unit is configured to cause the pump light to enter the vapor cell in a first direction parallel to the surface of the head of the subject,
the probe light emission unit is configured to cause the probe light to enter the vapor cell in a second direction perpendicular to the first direction,
the reflection unit is configured to reflect the probe light passed through the vapor cell, and
the polarization change detection unit is configured to detect the change in polarization of the probe light reflected by the reflection unit.

5. The magnetoencephalography meter according to claim 1,
wherein the laser light emission unit is configured to cause the laser light to enter the vapor cell in the −z direction toward the head of the subject which is a direction perpendicular to the surface of the head of the subject.

* * * * *